United States Patent [19]

Sitzmann et al.

[11] 4,449,000
[45] May 15, 1984

[54] 1:1:2 AND 1:3 MIXED POLYNITROETHYL ORTHOCARBONATES VIA MIXED TRIALKOXYMETHYL TRICHLOROMETHYL DISULFIDES

[75] Inventors: Michael E. Sitzmann, Adelphi; William H. Gilligan, Fort Washington, both of Md.

[73] Assignee: The United States of America as represented by the Secretary of the Navy, Washington, D.C.

[21] Appl. No.: 467,714

[22] Filed: Feb. 18, 1983

[51] Int. Cl.³ .................... C07C 79/343; C07C 76/02
[52] U.S. Cl. ................................ 568/22; 568/590; 149/88
[58] Field of Search .......................... 568/590, 22

[56] References Cited

U.S. PATENT DOCUMENTS 2,553,777 5/1951 Hawley et al. ............... 568/22 X
3,306,939 2/1967 Hill ................................... 568/590
3,388,147 6/1968 Kamlet et al. .............. 568/590 X

*Primary Examiner*—Bernard Helfin
*Attorney, Agent, or Firm*—Robert F. Beers; Kenneth E. Walden; Roger D. Johnson

[57] ABSTRACT

A 1:1:2 mixed orthocarbonate of the formula

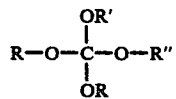

wherein
R and R″ are each one of the following groups
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), and
—CH$_2$CF$_3$, and R′ is one of the following
CH$_2$CF(NO$_2$)$_2$,
CH$_2$CF$_2$(NO$_2$), and
CH$_2$CF$_3$, provided that R≠R′, R≠R″, and R′≠R″. These 1:1:2 orthocarbonates are produced by the following reaction sequence:

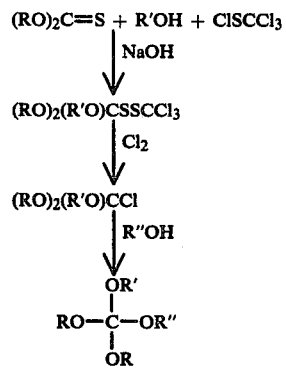

wherein R, R′, and R″ are as defined above.

By choosing R and R″ to be the same and either —CH$_2$(NO$_2$)$_2$CH$_3$ or —CH$_2$C(NO$_2$)$_3$ in the above reaction, 1:3 mixed orthocarbonates of the formula

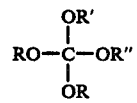

wherein R≠R′, R″≠R′, R=R″, and R and R″ are each
CH$_2$C(NO$_2$)$_2$CH$_3$,
CH$_2$C(NO$_2$)$_3$,
CH$_2$CF$_2$(NO$_2$), or
CH$_2$CF$_3$, and R′ is CH$_2$CF(NO$_2$)$_2$, CH$_2$CF$_2$(NO$_2$) or CH$_2$CF$_3$ may be prepared.

21 Claims, No Drawings

1:1:2 AND 1:3 MIXED POLYNITROETHYL ORTHOCARBONATES VIA MIXED TRIALKOXYMETHYL TRICHLOROMETHYL DISULFIDES

BACKGROUND OF THE INVENTION

This invention relates to organic orthocarbonates and more particularly to organic polynitro orthocarbonates.

In the early 1950's, M. E. Hill and coworkers at the Naval Ordnance Laboratory found that certain nitroalcohols would react with carbon tetrachloride in the presence of anhydrous ferric chloride to yield

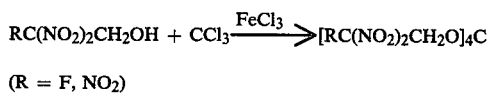

(R = F, NO₂)

symmetrical orthocarbonates. (e.g., see U.S. Pat. No. 3,306,939 entitled "Orthoesters of 2,2,2-Trinitroethanol," which issued to Marion E. Hill on Feb. 28, 1967.) However, the reaction is of very limited synthetic value for energetic orthocarbonates as only three nitroalcohols (2-fluoro-2,2-dinitroethanol, 2,2,2-trinitroethanol and 2,2-dinitropropane-1,3-diol) have been successfully used. With other nitroalcohols side reactions predominate and the principal product is the carbonate. Another drawback to Hill's method is that only symmetrical and no "mixed" orthocarbonates can be prepared. In a previous patent application filed by William H. Gilligan, 2:2 mixed fluoro-, nitro- and fluoronitroalkyl orthocarbonates were disclosed. Also, U.S. patent application Ser. No. 476,713, entitled "1:3 mixed polynitroethyl orthocarbonates from Tris(2-fluoro-2,2-dinitroethyl) Methyl Trichloromethyl Disulfide," filed by Michael E. Sitzmann and William H. Gilligan simultaneously with the present application Feb. 18, 1983, discloses 1:3 mixed orthocarbonates of the formula [CF(NO₂)₂CH₂O]₃—C—OR wherein R is a nitroalkyl group which is not CF(NO₂)₂CH₂—. The method as described is limited to the

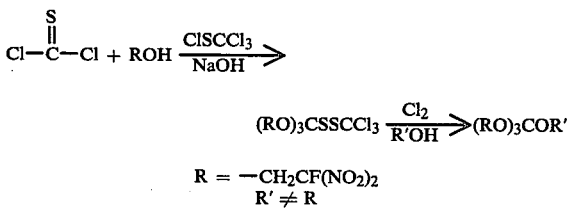

R = —CH₂CF(NO₂)₂
R' ≠ R preparation of a symmetrical trialkoxymethyl trichloromethyl disulfide in which all the alkoxy groups (RO) are identical. The symmetrical disulfide is chlorinated and treated with a second type of alcohol (R'OH) to give the 1:3 "mixed" orthocarbonate. 1:1:2 "mixed" orthocarbonates cannot be prepared by the method. In addition, the method as described is applicable only for 1:3 "mixed" orthocarbonates where ROH does not readily undergo reverse Henry reaction and thus is stable to the basic reaction conditions under which the symmetrical disulfide is formed.

SUMMARY OF THE INVENTION

Accordingly, an object of this invention is to provide novel organic compounds.

Another object of this invention is to provide novel 1:1:2 mixed polynitroorthocarbonates.

A further object of this invention to provide new high energy, high density explosive materials.

Yet another object of this invention is to provide new melt castable explosives.

A still further object of this invention is to provide new intermediates for the preparation of novel explosive compounds.

An additional object of this invention is to provide new high energy plasticizers.

Another object of this invention is to provide a new method of synthesizing novel explosive compounds.

These and other objects of this invention are accomplished by providing a 1:1:2 mixed orthocarbonate of the formula

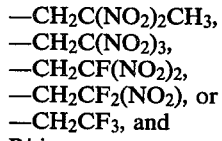

wherein
R and R" are each one of the following
—CH₂C(NO₂)₂CH₃,
—CH₂C(NO₂)₃,
—CH₂CF(NO₂)₂,
—CH₂CF₂(NO₂), or
—CH₂CF₃, and
R' is
—CH₃CF(NO₂)₂,
—CH₂CF₂(NO₂), or
—CH₂CF₃, provided that R≠R', R≠R", and R'≠R". These 1:1:2 orthocarbonates are produced by the following reaction sequence:

(RO)₂C=S + R'OH + ClSCCl₃    (Step 1)

↓ NaOH (RO)₂(R'O)CSSCCl₃    (Step 2)

↓ Cl₂

(RO)₂(R'O)CCl    (Step 3)

↓ R"OH

wherein R, R', and R" are as defined above.

By selecting the alcohol R'OH in step 3 of the above reaction sequence such that R=R", 1:3 orthocarbonates may be prepared. Of these, 1:3 orthocarbonates containing tris(2,2-dinitropropyl) or tris(2,2,2-trinitroethyl) moieties were not previously available.

DETAILED DESCRIPTION OF THE PREFERRED EMBODIMENT

The first step in preparing the 1:1:2 mixed orthocarbonates of this invention is to react a thionocarbonate of the formula

[RO]₂—C=S with an alcohol of the formula

R'OH and perchloromethyl mercaptan,

ClSCCl$_3$, in the presence of a hydroxyl ion source to produce a disulfide of the formula (RO)$_2$(R'O) CSSCCl$_3$.

The requirements are that R is
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), or
—CH$_2$CF$_3$;
and that R' is —CH$_2$CF(NO$_2$)$_2$,
—CH$_2$CF$_2$(NO$_2$), or
—CH$_2$F$_3$.

Thus the thionocarbonates used will be bis(2,2-dinitropropyl)thionocarbonate,

[CH$_3$C(NO$_2$)$_2$CH$_2$O]$_2$C=S;

bis(2,2,2-trinitroethyl)thionocarbonate,

[C(NO$_2$)$_3$CH$_2$O]$_2$C=S;

bis(2-fluoro-2,2-dinitroethyl)thionocarbonate,

[CF(NO$_2$)$_2$CH$_2$O]$_2$C=S;

bis(2,2-difluoro-2-nitroethyl)thionocarbonate,

[CF$_2$(NO$_2$)CH$_2$O]$_2$C=S;

and bis(2,2,2-trifluoroethyl)thionocarbonate,

[CF$_3$CH$_2$O]$_2$C=S.

Bis(2-fluoro-2,2-dinitroethyl)thionocarbonate can be prepared from 2-fluoro-2,2-dinitroethanol and thiophosgene using the method disclosed in U.S. Pat. No. 4,172,088 entitled, "Bis(2-fluoro-2,2-dinitroethyl)thionocarbonate and a Method of Preparation," which issued to Isaac A. Angres et al. on Oct. 23, 1979, herein incorporated by reference. The remaining thionocarbonates can be synthesized from thiophosgene and the appropriate alcohol using the method disclosed in U.S. Pat. No. 4,323,518 entitled "Polynitroethylthionocarbonates and Method of Preparation," which issued to William H. Gilligan on Apr. 6, 1982, herein incorporated by reference.

The alcohols (R'OH) used are
2-fluoro-2,2-dinitroethanol;

CF(NO$_2$)$_2$CH$_2$OH;

2,2,-difluoro-2-nitroethanol,

CF$_2$(NO$_2$)CH$_2$OH; and 2,2,2-trifluoroethanol,

CF$_3$CH$_2$OH.

Each of these alcohols are stable and will not deformylate in the presence of a base (OH$^-$ ions) but rather will form the ethoxy ions
CH(NO$_2$)$_2$CH$_2$O$^-$,
CF$_2$(NO$_2$)CH$_2$O$^-$, and
CF$_3$CH$_2$O$^-$, respectively.

In contradistinction, the alcohols 2,2-dinitropropanol and 2,2,2-trinitroethanol deformylate rather than form ethoxy ions and are therefore excluded from this first step. Another requirement is that the alcohol is chosen so that R≠R'. In other words, the alcohol used in this first step will not be the same as the alcohol that was used to make the thionocarbonate.

The thionocarbonate, alcohol, and perchloromethyl mercaptan are dissolved in a suitable solvent such as dichloromethane, 1,2-dichloroethane, or 1,1,2-trichloroethane. The reaction occurs as a strong hydroxyl ion source, preferably an alkali metal hydroxide, and more preferably NaOH or KOH, is slowly added at a rate such that the pH of the reaction mixture does not exceed 8. This is done to avoid the hydrolysis of thionocarbonates to carbonates which occurs in strongly basic solutions. The reaction temperature is preferably kept at from about 0° C. to about 5° C. by external cooling, agitation (e.g., stirring), and controlled addition of the hydroxyl ion source. Finally, a phase transfer catalyst is preferably used to speed up the reaction rate.

Phase transfer catalysts such as benzyltriethylammonium chloride, tetrabutylammonium chloride, didodecyldimethylammonium bromide, or cetyltrimethylammonium chloride may be used. The phase transfer catalyst is not consumed by the reaction; therefore only a small amount, a few mole percent, of the phase transfer catalyst is required.

Good discussions on the use of phase transfer catalysts are presented by Charles M. Starks, "Phase Transfer Catalysts. I. Heterogeneous Reactions Involving Anion Transfer by Quaternary Ammonium and Phosphonium Salts," Journal of the American Chemical Society, Volume 93:1, Jan. 13, 1971, pages 195–199, and by Echehard V. Dehmlow, "Phase-Transfer Catalyzed Two-Phase Reactions in Preparative Organic Chemistry," Angew. Chem. internat Edit. volume 13 (1974)/No. 3, Pages 170–178, adapted in Chemtech, April 1975, pages 210–218.

Examples 1, 2, and 3 further illustrate this step.

Next the disulfide (RO)$_2$(R'O)CSSCCl$_3$ formed in the previous reaction is reacted with chlorine to form the corresponding chloroorthoformate (RO$_2$)$_2$(R'O)CCl.

This can be accomplished by dissolving the disulfide in a suitable solvent (e.g., 1,2-dichloroethane) and then bubbling the chlorine gas into the solution. A preferred reaction temperature is from about 60° C. to about 70° C. Examples 4 through 9 further illustrate this step.

Next the chloroorthoformate is reacted with an alcohol of the formula R"OH, wherein R" is
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), or —CH$_2$CF$_3$,
and R″≠R and R″≠R′.

Thus the alcohol used in this third step will not be the same as the alcohol used in the first step or the alcohol used to form the thionocarbonate used in the first step. This step is preferably run at a temperature of from about 60° C. to about 70° C. If the alcohol R″OH used in step 3 will not react with chlorine gas, steps 2 and 3 may be combined by bubbling chlorine gas into a mixture of the disulfide (RO)$_2$(R′O)CSSCCl$_3$ and alcohol R″OH. The chloroorthoformate (RO)$_2$(R′O)CCl is formed and reacts in situ with the alcohol R″OH to form the 1:1:2 mixed orthocarbonate $$\begin{array}{c} OR' \\ | \\ RO-C-OR''. \\ | \\ OR \end{array}$$

Again, examples 4 through 9 further illustrate this procedure.

The solvents used in the above reactions are not critical. They are selected to meet conventional requirements such as inertness to the reactants, boiling points, ability to dissolve the reactants, etc. Preferred are chlorohydrocarbons such as dichloromethane, 1,2-dichloroethane, and 1,1,2-trichloroethane.

As discussed in the Background, Michael E. Sitzmann and William H. Gilligan (U.S. patent application Ser. No. 467,713 filed simultaneously with the present application on Feb. 18, 1983) disclose 1:3 mixed orthocarbonates based on the [CF(NO$_2$)$_2$CH$_2$O]$_3$C— moiety. That method of preparation could not be used to form 1:3 mixed orthocarbonates based on the

[CH$_3$C(NO$_2$)$_2$CH$_2$O]$_3$C— or

[C(NO$_2$)$_3$CH$_2$O]$_3$C— moieties because C(NO$_2$)$_3$CH$_2$OH and CH$_3$C(NO$_2$)$_2$C-H$_2$OH undergo reverse Henry reaction in strong base. The present process may be modified to produce these 1:3 orthocarbonates by using either (a) [CH$_3$C(NO$_2$)$_2$CH$_2$O]$_2$C=S for step 1 and CH$_3$C(NO$_2$)$_2$CH$_2$OH in step 3 or (b) [C(NO$_2$)$_3$CH$_2$O]$_2$C=S in step 1 and C(NO$_2$)$_3$CH$_2$OH in step 3 as the thionocarbonate and alcohol. All of the other conditions are kept the same as for the production of the 1:1:2 mixed orthocarbonate. The new 1:3 mixed orthocarbonates now possible are
[CH$_3$C(NO$_2$)$_2$CH$_2$O]$_3$C—OCH$_2$CF(NO$_2$)$_2$,
[CH$_3$C(NO$_2$)$_2$CH$_2$O]$_3$C—OCH$_2$CF$_2$(NO$_2$),
[CH$_3$C(NO$_2$)$_2$CH$_2$O]$_3$C—OCH$_2$CF$_3$,
[C(NO$_2$)$_3$CH$_2$O]$_3$C—OCH$_2$CF(NO$_2$)$_2$,
[C(NO$_2$)$_3$CH$_2$O]$_3$C—OCH$_2$CF$_2$(NO$_2$), and
[C(NO$_2$)$_3$CH$_2$O]$_3$C—OCH$_2$CF$_3$.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

Bis(2,2-dinitropropoxy) (2-fluoro-2,2-dinitroethoxy)methyl trichloromethyl disulfide (I)

A mixture of 20.5 g (0.06 mol) of bis(2,2-dinitropropyl)thionocarbonate, 14.5 g (0.078 mol) of perchloromethyl mercaptan and 21.2 g (0.138 mol) of 2-fluoro-2,2-dinitroethanol in 110 ml of methylene chloride was cooled in an ice-salt bath before 3.0 g of tetrabutyl ammonium chloride in 70 ml of water was added. 50% Aqueous sodium hydroxide (10.0 g) was diluted with 30 ml of water and added dropwise at 0° to 4° C. until the reaction solution turned basic to litmus paper. The methylene chloride layer was separated, dried and the solvent was removed to yield an oil which was washed with 200 ml of hexane and then with 200 ml of water. The insoluble oil was chromatographed on silica gel 60 (methylene chloride-hexane as eluent) to give 13.4 g (35%) of an oil which turned solid (mp 63–66) when triturated with hexane; H-NMR [(CD$_3$)$_2$C=O]: δ5.34 (d,2H), 4.91 (s,4H), 2.39 (s,6H).

Anal. calcd. for C$_{10}$H$_{12}$N$_6$FCl$_3$S$_2$O$_{15}$: C, 18.60; H, 1.87; N, 13.01; F, 2.94; Cl, 16.47; S, 9.93. Found: C, 18.80; H. 1.89; N, 12.96; F, 2.93; Cl, 16.50; S, 9.79.

EXAMPLE 2

Bis(2-fluoro-2,2-dinitroethoxy) (2,2,2-trifluoroethoxy)methyl trichloromethyl disulfide (II)

A solution of 10.5 g (0.03 mol) of bis(2-fluoro-2,2-dinitroethyl)thionocarbonate, 7.25 g (0.039 mol) of perchloromethyl mercaptan and 6.9 g (0.069 mol) of 2,2,2-trifluoroethanol in 50 ml of methylene chloride was cooled in an ice-salt bath. Tetrabutyl ammonium chloride (1.5 g) in 30 ml of water was added followed by the dropwise addition of a solution of 2.8 g of sodium hydroxide in 5 ml of water with cooling at 0° to 3° C. The methylene chloride layer was separated, dried and the volatiles were removed to give 16.5 g of oil which was extracted with 3X 50 ml of boiling hexanes. The cooled extracts were decanted from a small amount of oily precipitate and the solvent was removed to give 6.0 g (33%) of an oil which was nearly pure by thin-layered chromatographic (TLC) analysis. An analytical sample was obtained by column chromatography on silica gel 60 using hexane followed by methylene chloride-hexane as eluent; H-NMR (CDCl$_3$): 67 4.89 (d,4H), 4.15 (q, 2H).

Anal. calcd. for C$_8$H$_6$N$_4$F$_5$Cl$_3$S$_2$O$_{11}$: C, 16.02; H, 1.01; N, 9.34; F, 15.84; Cl, 17.74; S, 10.69. Found: C, 16.08; H, 1.02; N, 9.23; F, 15.63; Cl, 17.97; S, 10.81.

EXAMPLE 3

Bis(2,2,2-trifluoroethoxy) (2-fluoro-2,2-dinitroethoxy)methyl trichloromethyl disulfide (III)

To a well-stirred solution of 7.26 g (0.03 mol) of bis(2,2,2-trifluoroethyl)thionocarbonate, 6.14 g (0.033 mol) of perchloromethyl mercaptan and 6.0 g (0.039 mol) of 2-fluoro-2,2-dinitroethanol in 40 ml of methylene chloride cooled in an ice-salt bath was added 1.5 g of tetrabutyl ammonium chloride in 30 ml of water followed by the dropwise addition of 5 ml of 10 N aqueous sodium hydroxide at 0° to 5° C. The reaction solution was then kept slightly basic for 15 minutes by the addition of a few drops of aqueous sodium hydroxide when required. The methylene chloride layer was separated and the solvent was removed to give 18.0 g of oil which was dissolved in a small amount of chloroform and passed through a silica gel 60 column with methylene chloride-hexane (30:70) as eluent. The product was 9.95 g (61%) of an oil; H-NMR (CDCl$_3$): δ4.90 (d,2H), 4.15 (q, 4H).

Anal. calcd. for $C_8H_6N_2F_7Cl_3S_2O_7$: C, 17.61; H, 1.11; N, 5.13; F, 24.38; Cl, 19.49; S, 11.75. Found: C, 17.62; H, 1.05; N, 5.19; F, 24.17; Cl, 19.24; S, 11.56.

EXAMPLE 4

Bis(2,2-dinitropropyl)(2-fluoro-2,2-dinitroethyl) (2,2,2-trifluoroethyl)orthocarbonate (IV)

A solution of 2.15 g (0.0033 mol) of bis(2,2-dinitropropoxy) (2-fluoro-2,2-dinitroethoxy)methyl trichloromethyl disulfide in 7 ml of dry 1,2-dichoroethane was treated with chlorine gas at 60° C. for 1.5 hours before 4 ml of 2,2,2-trifluoroethanol was added. The solution was then heated at reflux temperature for 1.5 hours before the volatiles were removed and the residual oil was washed with hexane, then dissolved in chloroform and passed through a small silica gel 60 pad. Removal of the solvent gave 1.85 g (100%) of an oil: H-NMR (CDCl$_3$): δ4.68 (d,2H), 4.40 (s,4H), 3.92 (q,2H), 2.20 (s,6H).

Anal. calcd. for $C_{11}H_{14}N_6F_4O_{16}$: C, 23.50, H, 2.51; N, 14.95; F, 13.52. Found: C, 23.50; H, 2.61; N, 14.79; F, 13.57.

EXAMPLE 5

Tris (2,2-dinitropropyl) (2-fluoro-2,2-dinitroethyl)orthocarbonate (V)

Chlorine gas was passed into a solution of 2.15 g (0.0033 mol) of bis(2,2-dinitropropoxy) (2-fluoro-2,2-dinitroethoxy)methyl trichloromethyl disulfide and 1.10 g (0.0073 mol) of 2,2-dinitropropanol in 6 ml of dry 1,2-dichloroethane for 2 hours at 60° C. Heating at 60° C. was continued for 22 hours before the volatiles were removed and the solid residue was washed with hexane and then with water to give 2.14 g, mp 114°–118° C. Two crystallizations from 1.2-dichloroethane gave 1.79 g (89%), mp 129°–131° C.; H-NMR [(CD$_3$)$_2$C=O]: δ5.15 (d,2H), 4.71 (s,6H), 2.35 (s,9H).

Anal. calcd. for $C_{12}H_{17}N_8FO_{20}$: C, 23.54; H, 2.80; N, 18.30; F, 3.10. Found: C, 23.59; H, 2.82; N, 18.16; F, 3.07.

EXAMPLE 6

Bis(2,2-dinitropropyl) (2-fluoro-2,2-dinitroethyl) (2,2,2-trinitroethyl)orthocarbonate (VI)

A solution containing 1.85 g (0.0029 mol) of bis(2,2-dinitropropoxy) (2-fluoro-2,2-dinitroethoxy)methyl trichloromethyl disulfide and 1.04 g (0.00574 mol) of 2,2,2-trinitroethanol in 5 ml of dry 1,2-dichloroethane was chlorinated at 65° C. for 2 hours and then held at 65° for an additional 43 hours. The solvent was removed to give an oil which was stirred with hexane and then water to give 1.69 g of solid, mp 80°–90° C. Crystallization from chloroform gave 1.36 g (74%), mp 115°–117° C.; H-NMR [(CD$_3$)$_2$C=O]: δ5.50 (s, 2H), 5.20 (d, 2H), 4.76 (s, 4H), 2.36 (s, 6H).

Anal. calcd. for $C_{11}H_{14}N_9FO_{22}$: C, 20.54; H, 2.19; N, 19.60; F, 2.95. Found: C, 20.57; H, 2.23; N, 19.58; F, 3.02.

EXAMPLE 7

Bis(2-fluoro-2,2-dinitroethyl) (2,2,2-trinitroethyl) (2,2,2-trifluoroethyl)orthocarbonate (VII)

Chlorine gas was passed into a solution of 1.0 g (0.0017 mol) of bis(2-fluoro-2,2-dinitroethoxy) (2,2,2-trifluoroethoxy)methyl trichloromethyl disulfide and 0.62 g (0.0034 mol) of 2,2,2-trinitroethanol in 5 ml of dry 1,2-dichloroethane at 65° C. for 2 hours. Heating was continued at 65° C. for 50 hours before the solvent was removed and the residue (oil) was washed with hexane and then with water. The semisolid product was again washed with hexane and water to give 0.81 g (82%), mp 39°–41° C. Crystallization from chloroform-hexane raised the melting point to 41.5°–42.4° C.; H-NMR (CDCl$_3$): δ4.88 (s, 2H), 4.75 (d, 4H), 4.01 (q,2H).

Anal. calcd. for $C_9H_8N_7F_5O_{18}$: C, 18.10; H, 1.35; N, 16.42; F, 15.91. Found: C, 18.27; H, 1.34; N, 16.23; F, 15.78.

EXAMPLE 8

Bis(2-fluoro-2,2-dinitroethyl) (2,2-dinitropropyl) (2,2,2-trifluoroethyl)orthocarbonate (VIII)

A solution of 1.0 g (0.0017 mol) of bis(2-fluoro-2,2-dinitroethyoxy) (2,2,2-trifluoroethoxy)methyl trichloromethyl disulfide and 0.57 g (0.0038 mol) of 2,2-dinitropropanol in 6 ml of dry 1,2-dichloroethane was treated with chlorine gas at 60° C. for 2 hours, then held at 60°–64° C. for 46 hours. The solvent was removed and the residue was washed with hexane and water to give 0.97 g (100%) of an oil which was essentially pure by thin-layer chromatographic (TLC) analysis. Column chromatography on silica gel 60 (methylene chloride-hexane as eluents) gave 0.80 g (83%) of an analytically pure sample (oil); H-MNR (CDCl$_3$): δ4.67 (d, 4H), 4.40 (s,2H), 3.92 (q, 2H), 2.18 (s, 3H).

Anal. calcd. for $C_{10}H_{11}N_6F_5O_{16}$: C, 21.21; H, 1.96; N, 14.84; F, 16.78. Found: C, 21.28; H, 1.97; N, 14.61; F, 16.54.

EXAMPLE 9

Bis(2,2,2-trifluoroethyl) (2-fluoro-2,2-dinitroethyl) (2,2,2-trinitroethyl)orthocarbonate (IX)

Chlorine gas was passed into a solution of 3.60 g (0.0066 mol) of bis(2,2,2-trifluoroethoxy) (2-fluoro-2,2-dinitroethoxy)methyl trichloromethyl disulfide and 2.4 g (0.0132 mol) of 2,2-dinitroethanol in 10 ml of dry 1,2-dichloroethane at 60° C. for 2 hours. The solution was held at 60° C. for 48 hours before the solvent was removed and the residual oil was washed with hexane and then with water to give 3.44 g (96%) of an oil (essentially pure by TLC analysis). Column chromatography on silica gel 60 (methylene chloride-hexane as eluent) gave 2.92 g (82%) of analytically pure product (oil); H-NMR (CDCl$_3$): 4.86 (s, 2H), 4.74 (d, 2H), 3.98 (q, 4H).

Anal. calcd. for $C_9H_8N_5F_7O_{14}$: C, 19.90; H, 1.48; N, 12.89; F, 24.48. Found: C, 20.02; H, 1.50; N, 12.64; F, 24.43.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. A 1:1:2 mixed orthocarbonate of the formula

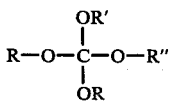

wherein
R and R'' are selected from the group consisting of
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), and
—CH$_2$CF$_3$,
and R' is selected from the group consisting of
CH$_2$CF(NO$_2$)$_2$,
CH$_3$CF$_2$(NO$_2$), and
CH$_2$CF$_3$,
provided that R≠R', R≠R'', and R'≠R''.

2. The 1:1:2 mixed orthocarbonate of claim 1 which is Bis(2,2-dinitropropyl) (2-fluoro-2,2-dinitroethyl) (2,2,2-trifluoroethyl)orthocarbonate.

3. The 1:1:2 mixed orthocarbonate of claim 1 which is Bis(2,2-dinitropropyl) (2-fluoro-2,2-dinitroethyl) (2,2,2-trinitroethyl)orthocarbonate.

4. The 1:1:2 mixed orthocarbonate of claim 1 which is Bis(2-fluoro-2,2-dinitroethyl) (2,2,2-trinitroethyl) (2,2,2-trifluoroethyl)orthocarbonate.

5. The 1:1:2 mixed orthocarbonate of claim 1 which is Bis(2-fluoro-2,2-dinitroethyl) (2,2-dinitropropyl) (2,2,2-trifluoroethyl)orthocarbonate.

6. The 1:1:2 mixed orthocarbonate of claim 1 which is Bis(2,2,2-trifluoroethyl) 2-fluoro-2,2-dinitroethyl) (2,2,2-trinitroethyl)orthocarbonate.

7. A 1:3 mixed orthocarbonate of the formula

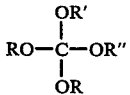

wherein
R=R'', R≠R', and R'≠R'' and R and R'' are selected from the group consisting of
—CH$_2$C(NO$_2$)$_2$CH$_3$,
—CH$_2$C(NO$_2$)$_3$,
—CH$_2$CF$_2$(NO$_2$), and
—CH$_2$CF$_3$,
and R' is selected from the group consisting of
—CH$_2$CF(NO$_2$)$_2$,
—CH$_2$CF$_2$(NO$_2$), and
—CH$_2$CF$_3$.

8. The 1:3 mixed orthocarbonate of claim 7 wherein R is —CH$_2$C(NO$_2$)$_3$.

9. The 1:3 mixed orthocarbonate of claim 7 wherein R is —CH$_2$C(NO$_2$)$_2$CH$_3$.

10. The 1:3 mixed orthocarbonate of claim 9 which is tris(2,2-dinitropropyl) (2-fluoro-2,2-dinitroethyl)orthocarbonate.

11. A disulfide of the formula

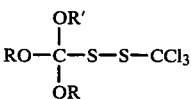

wherein

R≠R' and R is selected from the group consisting of
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), and
—CH$_2$CF$_3$,
and R' is selected from the group consisting of
CH$_2$CF(NO$_2$)$_2$,
CH$_2$CF$_2$(NO$_2$), and
CH$_2$CF$_3$.

12. The disulfide of claim 11 wherein R is selected from the group consisting of —CH$_2$C(NO$_2$)$_2$CH$_3$ and —CH$_2$C(NO$_2$)$_3$.

13. The disulfide of claim 12 which is bis(2,2-dinitropropoxy) (2-fluoro-2,2-dinitroethoxy)methyl trichloromethyl disulfide.

14. The disulfide of claim 11 which is bis(2-fluoro-2,2-dinitroethoxy) (2,2,2-trifluoroethoxy)methyl trichloromethyl disulfide.

15. The disulfide of claim 11 which is bis(2,2,2-trifluoroethoxy) (2-fluoro-2,2-dinitroethoxy)methyl trichloromethyl disulfide.

16. A process for preparing 1:1:2 mixed orthocarbonates of the formula

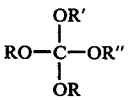

comprising the following steps in order:
(1) reacting a
(a) a thionocarbonate of formula (RO)$_2$C=S with (b) an alcohol of the formula R'OH and
(c) ClSCCl$_3$, in an 1:1:1 molar ratio in the presence of a hydroxyl ion source to produce a disulfide of the formula (RO)$_2$(R'O)CSSCCl$_3$;

(2) reacting the disulfide produced in step (1) with chlorine gas to produce a chloroorthoformate of the formula (RO)$_2$(R'O)CCl;

(3) reacting the chloroorthoformate produced in step (2) with an alcohol of the formula R''OH to produce the desired orthocarbonate of the formula

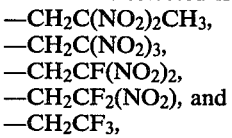

(4) isolating the product orthocarbonate;
wherein
R and R'' are selected from the group consisting of
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), and
—CH$_2$CF$_3$,
and R' is selected from the group consisting of $CH_2CF(NO_2)_2$,
$CH_2CF_2(NO_2)$, and
$CH_2CF_3$,
provided that $R \neq R'$, $R \neq R''$, and $R' \neq R''$.

17. The process of claim 16 wherein the hydroxyl ion source used in step (1) is an alkali metal hydroxide.

18. The process of claim 17 wherein the hydroxyl ion source is selected from the group consisting of NaOH and KOH.

19. The process of claim 16 wherein the reaction solution in step (1) is kept at a temperature of from about 0° C. to about 5° C.

20. The process of claim 16 wherein the reaction solution in step (2) is kept at a temperature in the range of from room temperature to about 70° C.

21. The process of claim 20 wherein the reaction solution in step (2) is kept at a temperature of from about 60° C. to about 70° C.

* * * * *